United States Patent [19]

Hamilton

[11] Patent Number: 4,823,625
[45] Date of Patent: Apr. 25, 1989

[54] CONTAMINANT SENSING SYSTEM

[76] Inventor: Samuel L. Hamilton, 3800 NW. 22nd Ave., Miami, Fla. 33142

[21] Appl. No.: 193,660

[22] Filed: May 13, 1988

[51] Int. Cl.$^4$ .......................................... G01M 19/00
[52] U.S. Cl. .................................. 73/866.5; 324/65 P; 340/631
[58] Field of Search ...................... 73/118.1, 866.5, 64; 340/631, 326, 331; 338/27, 28, 34; 324/65 P, 204

[56] References Cited

U.S. PATENT DOCUMENTS 3,432,750  3/1969  Botstiber ........................ 340/631 X
3,457,504  7/1969  Arthur et al. .................... 340/631 X Primary Examiner—Jerry W. Myracle
Attorney, Agent, or Firm—Fleit, Jacobson, Cohn & Price

[57] ABSTRACT

An annular absorbent filter element of a sensor probe is exposed to fluid while held by one end of a coil spring in contact with magnetic and non-magnetic discs non-conductively spaced from a third non-magnetic disc to supply a contamination signal to a two-stage detection circuit through which internal deterioration conditions of machinery are monitored. Electrically conductive and magnetic flux paths are established through the filter element and a flux gap to magnetically attract contaminants and establish parallel connected, variable resistances through which said contamination signal is derived. The signal output of the sensor probe thereby provides an early warning alert to prevent machinery damage.

10 Claims, 3 Drawing Sheets

# CONTAMINANT SENSING SYSTEM

BACKGROUND OF THE INVENTION

This invention relates generally to the monitoring of internal deterioration of machinery such as compressors, motors, engines, turbines, gear drives, etc., by detection of contaminants, including moisture and magnetic particles in fluids such as lubricating oil and refrigerant.

Internal deterioration of machinery has heretofore been monitored by physical examination of the filter media associated oil filters utilized to reduce wear of the machinery by recirculated wear particles. Magnetic probes involving the use of a permanent magnetic tip exposed to the fluid of the lubricating system of the machinery have also been utilized for some time to attract and hold magnetic particles. The magnetic particles so accumulated have been physically examined to determine the degree of wear involved.

Another known method of determining internal deterioration of machinery involves the spectral chemical analyses of the lubricating fluids. Such systems for monitoring the internal condition of machinery do not provide any determination as to the amount of free carbon in the lubricating oil and do not provide any indication of excess heat in the system.

Yet another known method of monitoring internal deterioration of machinery involves the microscopic examination of wear particles in samples of the lubricating fluid. None of the foregoing methods for monitoring machinery deterioration by examination of the circulating fluids provides an early warning of damage and shut down of the machinery before damage occurs.

Contamination of circulating fluids such as refrigerant and lubricating oil with moisture and associated contaminants such as acids resulting from chemical breakdown have heretofore been detected by means of sensor probes such as that disclosed in my prior U.S. Pat. No. 3,846,730, issued Nov. 5, 1974. According to such patent, the sensor probe exposed an absorbent material to the fluid causing a change in electrical resistance or conductivity thereof as a function of fluid contamination. The absorbent material is clamped between electrode discs and retained in place by an annular fabric element. One of the electrode discs is grounded while the other disc provides a resistance signal reflecting the level of contamination. According to my related U.S. Pat. No. 3,959,980, issued June 1, 1976, such resistance signal is fed to a two-stage detection system through which audio and visual alarm signals are generated and shutdown effected before equipment damage occurs.

It is therefore an important object of the present invention to provide an improved sensor probe and detection system for lubricating oil from which an analog signal is generated, the system being reversible to enable continuous monitoring with respect to a wide range of contaminants.

An additional object of the invention in accordance with the foregoing object is to provide early warning signals and/or shut down machinery prior to irreparable damage thereto in response to the aforementioned detection of fluid contamination.

SUMMARY OF THE INVENTION

In accordance with the present invention, the electrode discs of the sensor probe are axially spaced from each other by an insulating spacer. An annular fabric filter is seated on one of the discs and held thereon by one end portion of an electrically grounded spring in contact with another of the electrode discs for grounding thereof. Magnetic flux emitted from a pole face of a permanent magnet, mounted in abutment with a non-magnetic electrode disc, causes magnetic attraction of certain contaminants to the outer surface of the annular fabric filter element so that it establishes one conductive path to ground. Such magnetic attraction also entraps the contaminants in an axial flux gap between the grounded electrode disc and the non-magnetic electrode disc in order to establish another electrically conductive path to ground of variable resistance in parallel with first mentioned path.

The total variable resistance of the sensor probe controls the base bias levels applied in common to switching transistors in a two-stage detection system to control flashing operation of one visual indicator signifying excessive contamination. When excessive contamination is detected, a third visual indicator is continuously operated through a separately controlled switching transistor to provide the early warning of internal deterioration. Such continuous operation of the third visual indicator disables the first two visual indicators.

A horn is connected to operate intermittently and continuously with the second and third visual indicators, respectively, to provide an audio alarm. Interfacing relays are also energized simultaneously with the latter visual indicators to respectively provide inputs to a monitoring computer and effect shut down of equipment being monitored by the sensor probe.

These together with other objects and advantages which will become subsequently apparent reside in the details of construction and operation as more fully hereinafter described and claimed, reference being had to the accompanying drawings forming a part hereof, were in like numerals referred to like parts throughout.

BRIEF DESCRIPTION OF THE DRAWING FIGURES

DETAILED DESCRIPTION OF PREFERRED EMBODIMENT

Figure 1:
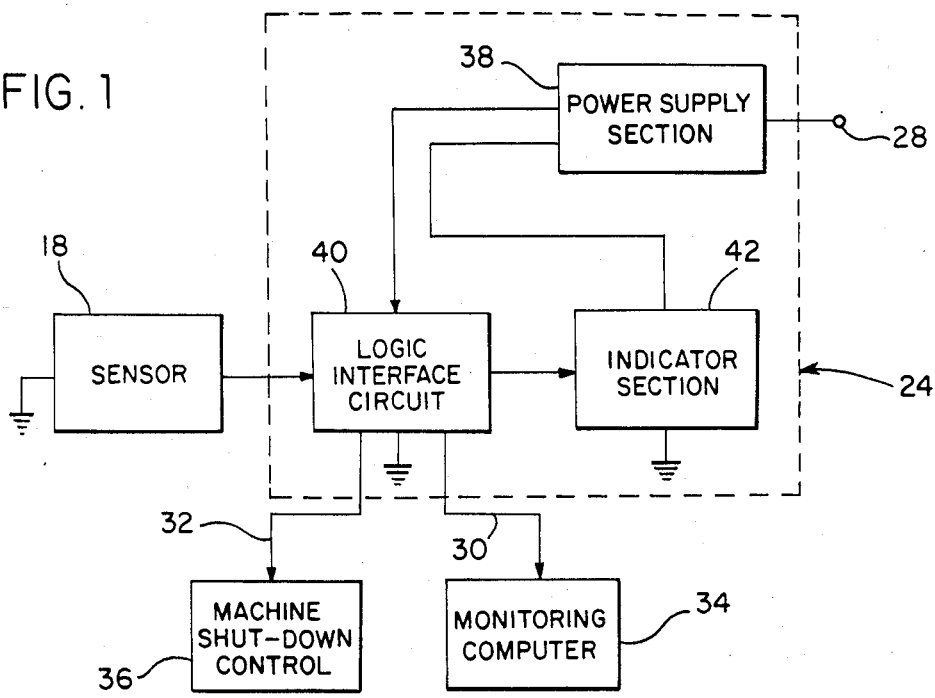
FIG. 1 is a block diagram schematically illustrating the system of the present invention.
Figure 2:
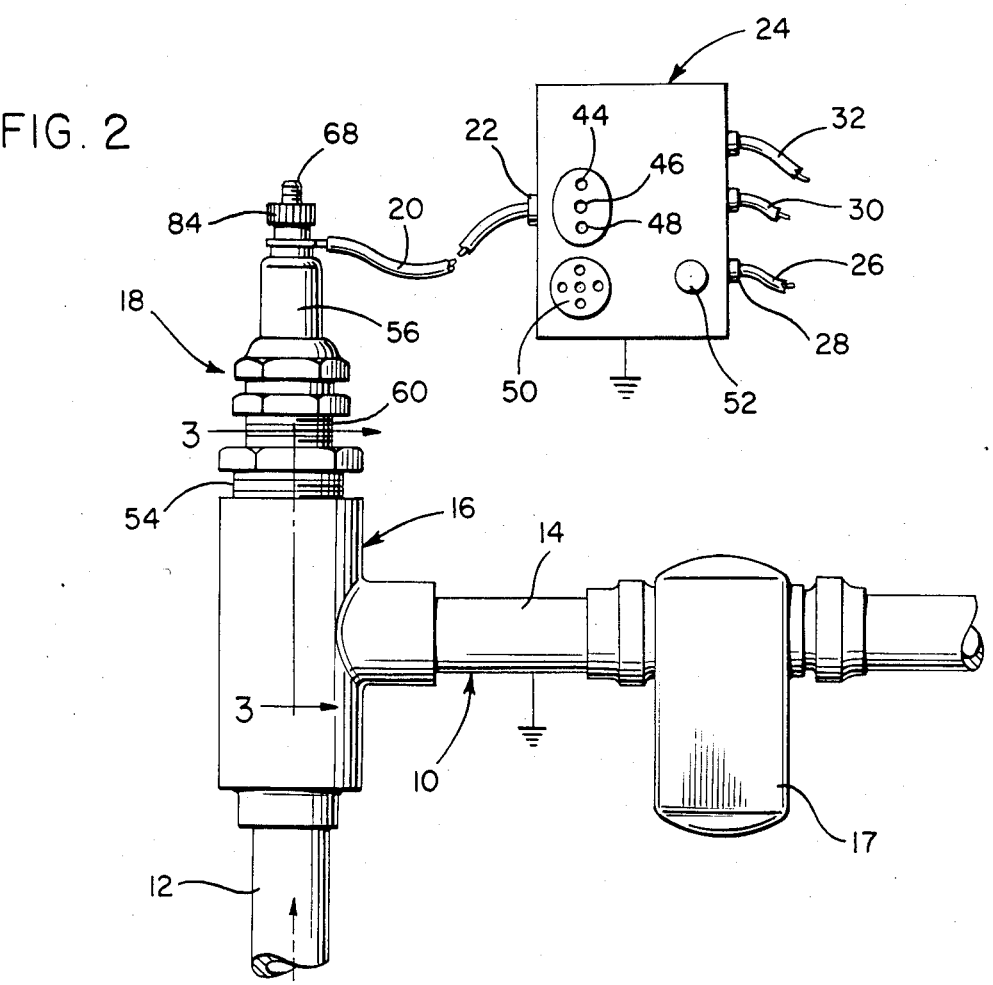
FIG. 2 is a partial elevation view of a typical installation of the present invention.

Referring now to the drawings in detail, FIG. 2 illustrates a typical installation 10 of the present invention including a probe assembly 18 mounted in a coupling fitting 16 which interconnects inflow conduit 12 and conduit section 14 conducting lubricating fluid through an oil filter 17. The sensor probe assembly 18 is electrically connected by an insulated single wire cable 20 to the signal input terminal 22 of a two-stage alarm console generally referred to by reference numeral 24. A power cable 26 connected to an available 110 VAC power source supplies power to the console 24 through power terminal 28. Signal output cables 30 and 32 connect the console to a signal monitoring computer 34 and a machine shutdown control 36, respectively, as diagrammed in FIG. 1.

The console 24 diagrammed in FIG. 1 includes a power supply section 38 from which power at an operating level is supplied to a two-stage logic circuit section 40 and an indicator section 42. The logic section receives the input through cable 20 from the sensor 18 and produces outputs applied to indicator section 42 and through signal cables 30 and 32 to the computer 34 and shutdown control 36. The indicator section 42 includes a bank of LED types of visual indicators 44, 46 and 48, as shown in FIG. 2, emitting flashing green and yellow lights and a red continuous light, respectively, to signify normal, early warning and shutdown conditions. A pulsating audio alarm is emitted simultaneously with the flashing yellow light from a horn 50. The visual indicators and audio alarm are all shown exposed on a panel of the console 24 with a replaceable power fuse 52.

The sensor 18 as shown in FIGS. 2, 3, 5 and 6 is mounted by means of a threaded bushing 54 in the body of the fitting 16. The sensor includes an elongated tubular plug 56 made of an insulative material such as porcelain, positioned within a mounting sleeve 60 threadably positioned within the bushing 54. The lower axial end of the sleeve 60 within bushing 54 is engaged by one end of a coil spring 62 positioned on the porcelain body 56 to contact and exert an axial bias on an annular magnetic electrode disc 64. The disc 64 is supported by a threaded end portion 66 of an elongated anode shaft 68 by means of an annular insulator 70. The anode shaft 68 is connected to cable 20 by terminal 84 as shown in FIG. 2.

Figure 3:
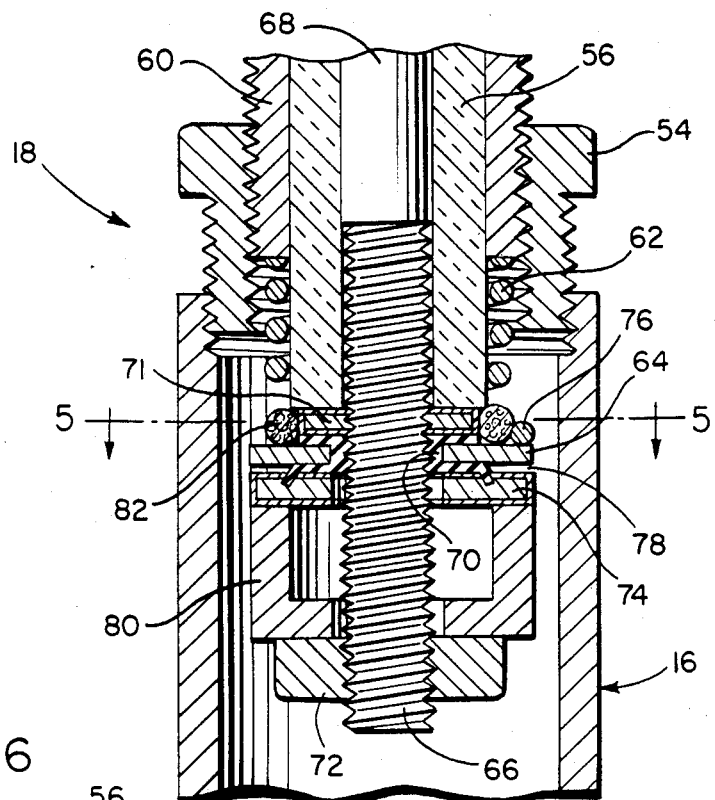
FIG. 3 is an enlarged partial sectional view taken substantially through a plane indicated by section line 3—3 in FIG. 2.
Figure 6:
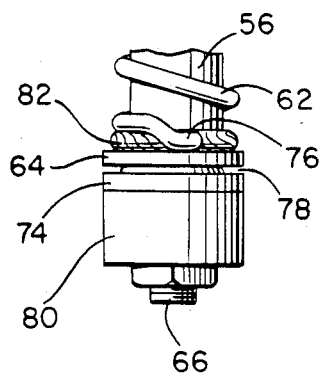
FIG. 6 is a partial sectional view taken substantially through a plane indicated by section line 6—6 in FIG. 5.

The insulator 70 is held axially assembled between a non-magnetic electrode disc 71 threadedly mounted on anode shaft 68 as shown in FIG. 3. The disc 71 abuts one end of porcelain body 56 and a non-magnetic electrode disc 74, under the axial bias of spring 62. A non-magnetic locknut 72 holds a cup-shaped permanent magnet 80 in abutment with disc 74. The discs 71 and 74 are plated with a corrosive resistant coating. The disc 71 is also diametrically smaller than the electrode discs 74 and 64 so as to form a radially outer edge seat for an annular absorbent filter element 82 retained thereon by an angularly extending end portion 76 of spring 62 in abutment with electrode disc 64. Accordingly, the annular element 82 acts as a variable resistor connected through one conductive path formed between discs 64 and 71 to ground. The resistance of the element 82 will vary with the contaminants and the fluid picked up or absorbed therein and its moisture content. A second conductive path is established by such contaminants in fluid through an axial gap 78 between electrode discs 64 and 74. Disc 74 is electrically connected to the anode shaft 68 by magnet 80, while disc 64 is electrically grounded through abutting coil spring 62 and fitting 16.

The annular filter element 82 of the sensor 18 is made of an absorbent fabric such as cotton string material commonly used for lubricating oil filters in centrifugal refrigeration equipment. The sensor may be installed either upstream of the lubricating oil filter 17 as shown in FIG. 2 or downstream thereof to detect contamination of lubricating oil in such equipment.

Figure 7:
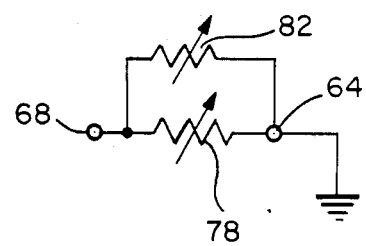
FIG. 7 is an electrical circuit diagram of an equivalent circuit corresponding to the sensor probe assembly shown in FIGS. 2, 3, 5 and 6.
Figure 5:
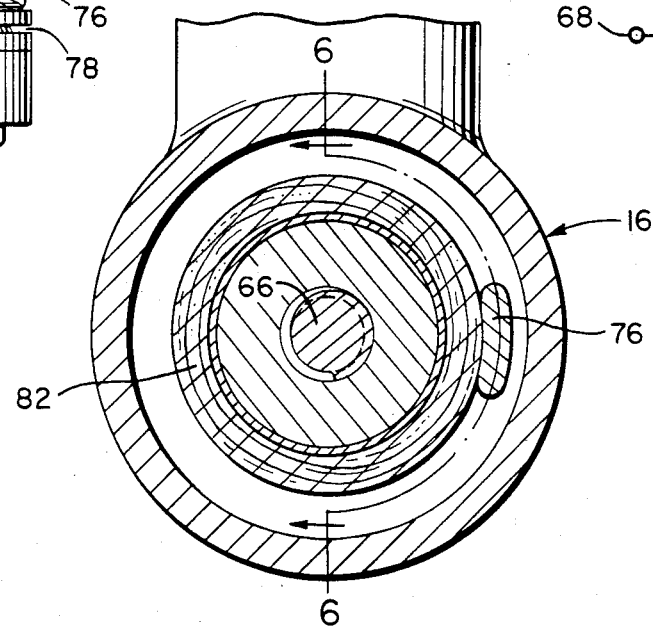
FIG. 5 is a transverse section view taken substantially through a plane indicated by a section line 5—5 in FIG. 3.

The sensing element 82 absorbs moisture and water solutions of emulsion and acid to conduct current and collects contaminants on its outer surface to vary its resistance of its conductive parts. Contaminants such as metals and carbon floating in the lubricating fluid being monitored are furthermore trapped and collected within gap 78 bridging discs 64 and 74 under the magnetic attraction of the magnetic field associated with the magnetic flux path established between the magnet 80 and the magnetic electrode disc 64. Such collection of contaminants will affect the conductivity of the conductive path through gap 78 connected in parallel with the conductive path through element 82 as diagrammed in FIG. 7. Thus, the total resistance of the sensor will be determined by the parallel connected paths of variable resistance as a function of the contamination being monitored.

Figure 4:
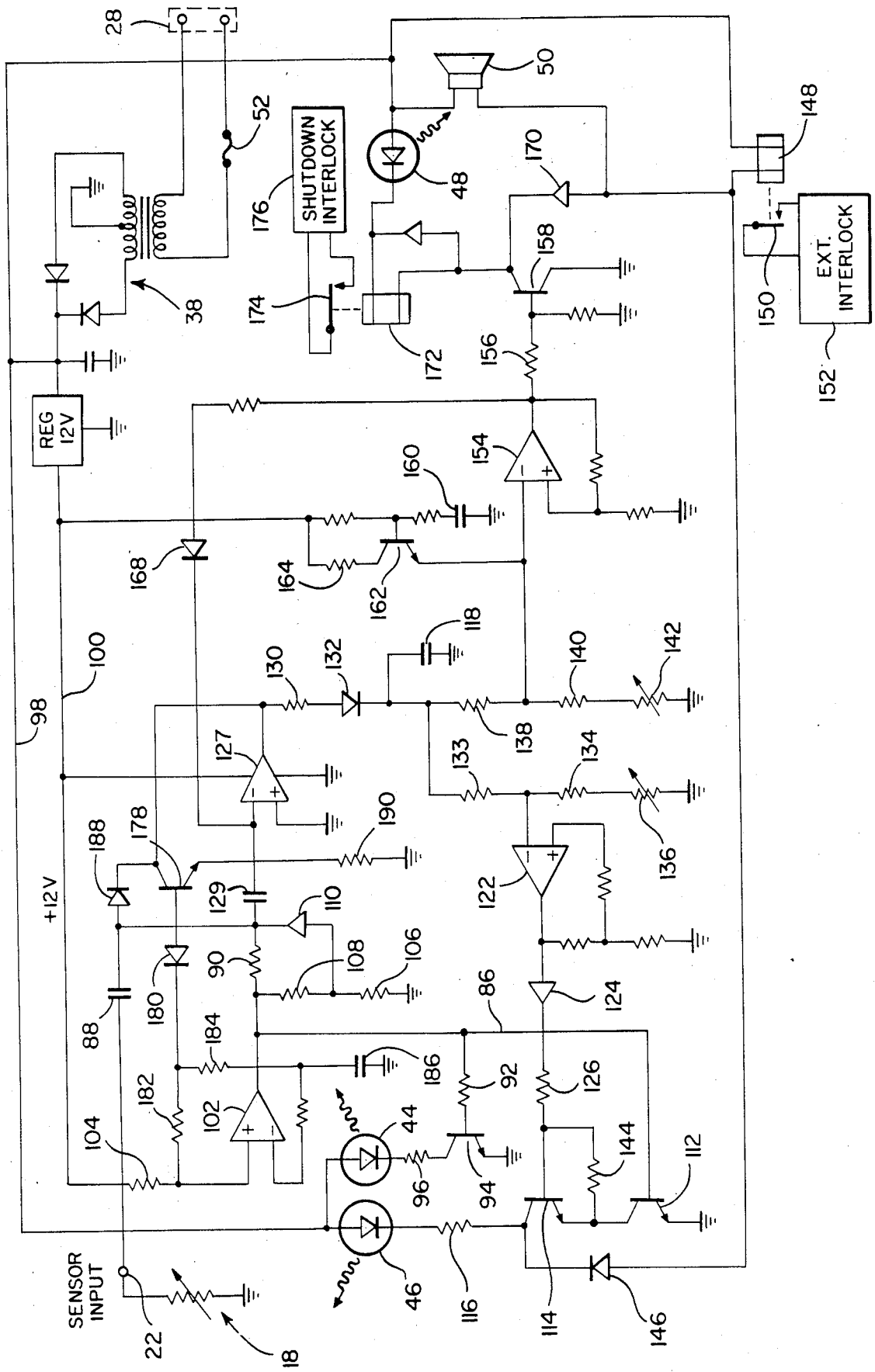
FIG. 4 is an electrical circuit diagram of the two-stage detection and indicator circuit of the present invention.

The sensor 18 is not only useful in providing audio and visual alarms in response to excessive fluid contamination, but is also an accurate source of input data for the contamination monitoring computer 34 aforementioned in connection with FIG. 1. As shown in FIG. 4, the sensor 18 represented as a variable resistor connected to the input terminal 22, conducts current to ground from the output of a detection amplifier 102 through resistor 90 and capacitor 88 in the circuit section 40. The output potential of amplifier 102 in line 86 is above a minimum level determined by resistors 106 and 108 and the voltage applied to the non-inverting input of the amplifier through resistor 104 from the lower regulated, dc voltage line 100 of the power supply section 38. Under normal conditions, a relatively high potential on line 86 from the output of amplifier 102 is applied through resistor 92 to the base of transistor 94 causing it to conduct and complete an energizing circuit through indicator lamp 44 in series with load resistor 96. The current when conducted by line 86 lowers the potential to a level determined by the voltage dividing resistors 10 and 108 and the inverter 110 until the transistor 94 is cut off and the indicator 44 is extinguished. Capacitor 88 will then recharge and reestablish the higher potential in line 86 as determined by the resistance of sensor 18. Thus, the cycle is repeated to cause flashing of the indicator lamp 44 reflecting the normal condition.

When the fluid contamination approaches an excessive level, a corresponding decrease in the resistance of sensor 18 occurs to reduce the cut-off potential on line 86 directly to the base of transistor 112 which is normally held non-conductive. Such reduction in the cut-off potential causes transistor 112 to switch on so as to complete an energizing circuit to ground through the LED indicator 46 in series with load resistor 116 and transistor 114 from the voltage line 98. Transistor 114 is normally maintained non-conductive by a bias potential applied from storage capacitor 118 connected to the base of transistor 114 through resistor 120, amplifier 122, inverter 124 and base resistor 126. Capacitor 118 is charged by the output of an amplifier 127 in series with resistor 90, capacitor 129, resistor 130 and diode 132 to a level determined by resistors 133, 134 and level adjustment control 136 connected in parallel above ground with resistors 138, 140 and level adjustment control 142. When transistor 112 is switched on, it also begins to discharge capacitor 118 through resistor 144 causing switch on of transistor 114 in a cyclic manner. The yellow light from LED indicator 46 will accordingly by emitted intermittently as a warning alert.

When transistor 114 is switched on, it also completes an energized circuit for horn 50 from voltage line 98 through diode 146. Thus, an intermittent audio alarm will be emitted simultaneously with the visual alert of LED indicator 46. A relay coil 148 is connected across the horn 50 so as to simultaneously close a normally open relay switch 150 operative through an external interlock 152 to supply an input to the monitoring computer.

When the resistance of sensor 18 reaches a dangerously low resistance value reflecting excessive fluid contamination, the charge level on capacitor 118 is correspondingly reduced to apply an input to amplifier 154 from the junction between resistors 138 and 140 producing an output which is applied through resistor 156 to the base of transistor 158 causing it to switch on. The operating potential at the input of amplifier 154 is maintained by discharge of previously charged capacitor 160 causing switch on of transistor 162. When switched on, transistor 162 applies the lower dc potential in line 100 through voltage reducing resistor 164 to the input of amplifier 154. At the same time, the output of amplifier 154 is applied through resistor 166 and diode 168 to the inverting input of amplifier 127 to maintain the low level charge on capacitor 118. Thus, transistor 158 will be maintained conductive to constantly energize the horn 50 connected in series with diode 170 between the voltage line 98 and the collector of transistor 158 having a grounded emitter. Connected in parallel with horn 50 and diode 170 is a relay coil 172 in series with red LED indicator 48. Thus, the indicator 48 and relay coil will be constantly energized simultaneously with horn 50. When energized, the relay coil 172 closes its relay switch 174 to effect machinery shut-down through interlock 176.

When the foregoing excessive contamination alarm condition occurs, the constant output of amplifier 127 maintains a switch-on bias on the collector of transistor 178 having its base connected through diode 180 to the junction of voltage dividing resistors 182 and 184 respectively connected to the input of amplifier 102 and grounded capacitor 186. With transistor 178 switched on, capacitor 88 is discharged to ground through diode 88 and resistor 190. As a result, indicators 44 and 46 are disabled for the duration of the excessive contamination alarm condition.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. In combination with a fluid contamination sensor having axially spaced discs and an absorbent element held in contact with two of said discs to establish a conductive path of variable resistance therethrough, means for seating the absorbent element in abutment with said two of the discs radially outward of one of the two discs and means for insulating said two of the discs from each other radially inwardly of the absorbent element.

2. The combination of claim 1 including two visual indicators and a shut-down control device, alarm control means electrically connected to said conductive path in the sensor for continuously energizing one of said indicators during operation thereof and intermittently energizing the other of the indicators during operation thereof, and means for disabling operation of the other of the indicators during said continuous energization of said one of the indicators.

3. The combination of claim 2 further including a third indicator and means responsive to detection of normal conditions by the sensor for intermittently energizing the third indicator.

4. The combination as defined in claim 3 including a monitoring computer and means responsive to said operation of the other of the indicators for transmitting an input to the monitoring computer.

5. The combination of claim 1 wherein the other of the two discs is electrically grounded.

6. The combination of claim 1 including magnetic means for effecting magnetic attraction of contaminants on the absorbent element.

7. The combination of claim 1 wherein a third of said axially spaced discs is non-conductively spaced by the insulating means from the two of said discs forming a gap within which a second conductive path of variable resistance is established in parallel with the first mentioned path.

8. In combination with a variable resistance sensor and a detection system connected thereto having at least two indicators, alarm control means responsive to a decrease in resistance of the sensor from a normal level for energizing the two indicators in sequence intermittently and continuously, respectively, means responsive to said continuous energization of one of the two indicators for disabling the other of the two indicators, a third indicator and means for intermittently energizing the third indicator in response to said normal resistance level of the sensor, said sensor including a pair of discs, means mounting said discs in axially spaced relation to each other, a non-conductive spacer in axial abutment between said discs, an absorbent element seated on one of said discs and means holding the absorbent element on the other of the discs and electrically grounding the same for rendering the absorbent element operative as a reversible variable resistor electrically interconnecting the discs.

9. In combination with a fluid contamination sensor having axially spaced discs and an absorbent filter, means in abutment with one of said discs for establishing a magnetic field through which an electrically conductive path extends and means holding the filter seated on one of the discs for establishing another electrically conductive path therethrough in parallel with said first mentioned path within the magnetic field.

10. The combination of claim 9 wherein said holding means includes a magnetic electrode spaced from said one of the discs by a magnetic flux gap through which said first mentioned conductive path extends and an electrically conductive spring having an end portion in abutment with said magnetic electrode and engaging the absorbent filter radially outward of said one of the discs on which the filter is seated.

* * * * *